(12) United States Patent
Carlson

(10) Patent No.: US 11,759,409 B2
(45) Date of Patent: *Sep. 19, 2023

(54) COSMETIC MATERIAL COMPOSITION

(71) Applicant: Tygrus, LLC, Troy, MI (US)

(72) Inventor: Lawrence Carlson, Oxford, MI (US)

(73) Assignee: Tygrus, LLC, Troy, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/068,259

(22) Filed: Oct. 12, 2020

(65) Prior Publication Data

US 2021/0022971 A1    Jan. 28, 2021

Related U.S. Application Data

(63) Continuation of application No. 15/476,336, filed on Mar. 31, 2017, now Pat. No. 10,799,437.

(60) Provisional application No. 62/316,479, filed on Mar. 31, 2016.

(51) Int. Cl.
| | | |
|---|---|---|
| *A61K 8/19* | (2006.01) | |
| *A61K 8/362* | (2006.01) | |
| *A61K 8/24* | (2006.01) | |
| *A61Q 17/00* | (2006.01) | |
| *A61K 8/23* | (2006.01) | |
| *A61Q 19/08* | (2006.01) | |

(52) U.S. Cl.
CPC ............... *A61K 8/19* (2013.01); *A61K 8/23* (2013.01); *A61K 8/24* (2013.01); *A61K 8/362* (2013.01); *A61Q 17/005* (2013.01); *A61K 2800/52* (2013.01); *A61Q 19/08* (2013.01)

(58) Field of Classification Search
CPC ...................................................... A61K 8/19
See application file for complete search history.

(56) References Cited

U.S. PATENT DOCUMENTS

| | | | |
|---|---|---|---|
| 5,380,430 A | 1/1995 | Overton et al. | |
| 5,571,336 A | 11/1996 | Wurzburger et al. | |
| 5,575,974 A | 11/1996 | Wurzburger et al. | |
| 5,698,107 A | 12/1997 | Wurzburger et al. | |
| 5,756,051 A | 5/1998 | Overton et al. | |
| 5,830,838 A | 11/1998 | Wurzburger et al. | |
| 5,891,320 A | 4/1999 | Wurzburger et al. | |
| 5,895,782 A | 4/1999 | Overton et al. | |
| 6,096,222 A | 8/2000 | Wurzburger et al. | |
| 6,197,816 B1 | 3/2001 | Vincent et al. | |
| 7,513,987 B1 | 4/2009 | Wurzbarger | |
| 9,011,700 B2 | 4/2015 | Eng et al. | |
| 2001/0019728 A1 | 9/2001 | Basinger et al. | |
| 2002/0187203 A1 | 12/2002 | Cioca et al. | |
| 2009/0304608 A1 | 12/2009 | Cueman et al. | |
| 2016/0312093 A1 | 10/2016 | Carlson et al. | |
| 2017/0000114 A1 | 1/2017 | Carlson | |
| 2017/0281484 A1 | 10/2017 | Carlson | |
| 2017/0368556 A1 | 12/2017 | Carlson | |

FOREIGN PATENT DOCUMENTS

| | | |
|---|---|---|
| CH | 706747 A2 | 1/2014 |
| CN | 102747371 A | 10/2012 |
| EP | 2347797 A2 | 7/2011 |
| RU | 2091321 C1 | 9/1997 |
| RU | 2142930 C1 | 12/1999 |
| RU | 2174959 C1 | 10/2001 |
| RU | 2284966 C2 | 10/2006 |
| RU | 2476804 C2 | 2/2013 |
| WO | 1998/05595 A1 | 2/1998 |
| WO | 2001/034754 A1 | 5/2001 |
| WO | 2005113735 A1 | 12/2005 |

OTHER PUBLICATIONS

International Search Report and Written Opinion for international application No. PCT/US2017/039241; dated Oct. 5, 2017; ISA/RU; 7 pages.
Chang-Geng Ding, et al., "Partially and Fully Deprotonated Sulfuric Acid", Chemical Physics Letters, vol. 390, No. 4-6, Apr. 30, 2004, pp. 307-313.
Orkid Coskuner, et al., "Water Dissociation in the Presence of Metal Ions", Angewandte Chemie, vol. 119, No. 41, Oct. 15, 2007, pp. 7999-8001.
Supplementary European Search Report, EP16784073, dated Dec. 20, 2018, 5 pages.
Supplementary European Search Report for EP 16821874, dated Dec. 20, 2018, 3 pages.
Steposol DG, Stepan, Proprietary Cationic/Nonionic Blend, retreived from the Internet, dated Apr. 1, 2009, @BULLET Highway Structures, 2 pages.
Stepan Company, Safety Data Sheet, "Steposol DG", retreived from the internet, dated Jan. 1, 2014, 8 pages.

(Continued)

*Primary Examiner* — Benjamin J Packard
(74) *Attorney, Agent, or Firm* — Young Basile Hanlon & MacFarlane, P.C.

(57) ABSTRACT

A composition comprising:
at least one compound of the chemical structure:

$$\left[ H_x O_{\frac{(x-1)}{2}} \right] Z_y$$

wherein x is and odd integer ≥3;
y is an integer between 1 and 20; and
Z is one of a monoatomic ion from Groups 14 through 17 having a charge value between −1 and −3 or a polyatomic ion having a charge between −1 and −3; or $$Z'\text{—}H_{x'}O_{x'-y'}$$

wherein x' is and integer greater than 3
y' is an integer less than x'; and
Z' is one of a monoatomic cation, a polyatomic ion or a cationic complex;
and
at least one of a humectant emollient or carrier.

10 Claims, No Drawings

(56) References Cited

OTHER PUBLICATIONS

International Preliminary Report on Patentability, for international application No. PCT/US2017/039241, dated Jan. 3, 2019, 6 pages.
Supplementary European Search Report in corresponding application EP17776826, dated Dec. 2, 2019, 7 pages.

COSMETIC MATERIAL COMPOSITION

The present application is a continuation of U.S. Nonprovisional patent application Ser. No. 15/476,336 which is currently pending and claims priority to U.S. Provisional Application Ser. No. 62/316,479 filed Mar. 31, 2016, the specifications of which are incorporated in their entirety herein.

BACKGROUND

The present invention relates to cosmetic compositions exhibiting antimicrobial attributes and/or those having enhanced shelf stability.

Cosmetic materials are compositions or articles that can be rubbed, sprinkled, sprayed on introduced into or otherwise or otherwise applied to the human body for beautifying, promoting attractiveness or altering appearance. It is necessary that cosmetic products be safe and effective for use or application on an individual. Recently, there has been a growing movement toward the use of organic and sustainable non-synthetic products in various cosmetics and toiletries and to providing cosmetics and toiletries in which many, if not all, of the constituent components are naturally derived. There is also a great demand for removing harsh synthetic stabilizers and preservatives from cosmetic compositions.

It has also become increasingly desirable to provide cosmetic compositions that provide a source of hydrogen in a form that is more readily available for uptake by cells of the epidermis or cells of the epidermis and associated regions. It is believed by some compounds that potentially could supply a source of hydrogen in a dermally acceptable manner to enhance and support skin health can be incorporated into cosmetic products.

Thus, it would be desirable to provide a cosmetic composition that exhibits attributes of shelf stability and/or microbial resistance while reducing or eliminating the concentration of synthetic stabilizers and/preservatives present in the composition.

SUMMARY

Disclosed herein is a cosmetic composition comprising:
at least one carrier material;
at least one active agent; and
a compound having the following chemical structure:

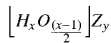

wherein x is and odd integer 3;
y is an integer between 1 and 20; and
Z is a polyatomic ion; or

where x is an integer greater than 3; and
wherein y is and integer less than x;
wherein the charge value associated with the molecular component is at least −1; and
at least one of a pigment, humectant, emollient, aqueous carrier or the like.

DETAILED DESCRIPTION

It has been long accepted scientific fact that, based upon laws of thermodynamics, the internal energy of a closed system is stable when the two different charge-types, i.e. moles of positively charged cations (+) and moles of negatively charged anions (−), are stoichiometrically charge-balanced; yielding a stable charge neutral aqueous solution. It has been widely held that electrostatic charge types in a neutral solution will necessarily have positive electrostatic charges (+) balanced by an equal number of negative (−) electrostatic charges. However studies conducted on aqueous acidic solutions indicate that various solutions may process and excess of acid proton ions.

This phenomenon supports the conclusion that water molecules are effective in stabilizing unbalanced charges present in solution. It is believed that water molecules present in an aqueous solution stabilize any unbalanced charges and to yield a charge balanced solution. The results conform to the laws of thermodynamics and point to the presence of a new type of charge balancing nucleophile composed of lone pair electrons of water molecules.

Disclosed herein is cosmetic composition that includes a novel compound that can broadly be classified as an electrolyte that can be employed in a suitable cosmetic composition. in certain applications to the novel component can be present in such cosmetic compositions in an aqueous solution component thereof. The compound incorporated in the cosmetic composition can be broadly construed as an oxonium ion-derived complex.

As defined herein "oxonium ion complexes" are generally defined as positive oxygen cations having at least one trivalent oxygen bond. In certain embodiments, the compound incorporated in the cosmetic composition will include at least one oxygen cation that will exist in aqueous solution as a population predominantly composed of one, two and three trivalently bonded oxygen cations present as a mixture of the aforesaid cations or as material having only one, two or three trivalently bonded oxygen cations. Non-limiting examples of oxonium ions complexes having trivalent oxygen cations can include hydronium ions.

It is contemplated that the in certain embodiments the oxygen cation will exist in aqueous solution as a population predominantly composed of one, two and three trivalently bonded oxygen anions present as a mixture of the aforesaid anions or as material having only one, two or three trivalently bonded oxygen anions The compound as disclosed herein can be admixed with an aqueous or polar solvent, the resulting composition is as solution canbecomposedofhydroniumions and/or hydroniumion complexes. Suitable cationic materials can alsobereferred to as hydroxoniumion complexes. The compound and solutions that contain the same may have utility in various applications where controlled pH and/or antimicrobial/bactericidal characteristics is desirable. It is also contemplated that the compound can function as a source of available hydrogen for cellular uptake by dermal and epidermal cells to which the cosmetic composition is applied. Non-limiting examples of such compositions include topical and cosmetic compositions. The materials disclosed herein may also have applicability situations not limited to in certain skin cleansing and/or nutrient supplying applications.

It has been theorized that extreme trace amounts of cationic hydronium may spontaneously form in water from water molecules in the presence of hydrogen ions. Without being bound to any theory, it is believed that naturally occurring stable hydronium ions are extremely rare, if they occur at all. The concentration of naturally occurring hydronium ions in water is estimated to be no more than 1 in 480,000,000. It is also theorized that naturally occurring hydronium ions are unstable transient species with lifespans typically in the range of nanoseconds. Naturally occurring hydronium ions are reactive and are readily solvated by water and as such these hydronium ions (hydrons) do not exist in a free state.

When introduced into pure water, the stable hydronium material disclosed herein will complex with water molecules to form hydration cages of various geometries, non-limiting examples of which will be described in greater detail subsequently. The stable electrolyte material as disclosed herein, when introduced into aqueous solution is stable and can be isolated from the associated water by processes that will be described in detail subsequently.

Strong organic and inorganic acids such as those having a $pK_a \geq 1.74$, when added to water, will ionize completely in the aqueous solution. The ions so generated will protonate existing water molecules to form $H_3O+$ and associated stable clusters. Weaker acids, such as those having a $pK_a <1.74$, when added to water, will achieve less than complete ionization in aqueous solution but can have utility in certain applications. Thus, it is contemplated that the acid material employed to produce the stable electrolyte material can be a combination of one or more acids. In certain embodiments, the acid material will include at least one acid having a $pK_a$ greater than or equal to 1.74 in combination with weaker acids(s).

In the present disclosure, it has been found quite unexpectedly that the stable hydronium electrolyte material as defined herein, when added to an aqueous solution, can produce a polar solvent material and can provide and effective $pK_a$ which is dependent on the amount of stable hydronium material added to the corresponding solution independent of the hydrogen ion concentration originally present in that solution. The resulting solution can function as a polar solvent and can have an effective $pK_a$ between 0 and 5 in certain applications when the initial solution pH prior to addition of the stable hydronium material is between 6 and 8 as measured by pH measurement devices such as those having high sensitivity calomel OPR, one non-limiting example of which is the Thermo-scientific Orion Star A-111.

It is also contemplated that the stable hydronium material as disclosed herein can be added to solutions having an initial pH in the more alkaline range, for example between 8 and 12 to effectively adjust the pH of the resulting solvent and/or the effective or actual $pK_a$ of the resulting solution. Addition of the stable electrolyte material as disclosed herein can be added to the alkaline solution without measurable reactive properties including but not limited to exothermicity oxidation or the like.

The acidity of theoretical hydronium ions existing in water as a result of aqueous auto-dissociation is the implicit standard used to judge the strength of an acid in water. Strong acids are considered better proton donors than the theoretical hydronium ion material otherwise a significant portion of acid would exist in a non-ionized state. As indicated previously, theoretical hydronium ions derived from aqueous auto-dissociation are unstable as a species, random in occurrence and believed to exist, if at all in extreme low concentration in the associated aqueous solution. Generally, hydronium ions in aqueous solution are present in concentrations between less than 1 in 480,000,000 and can be isolated, if at all, from native aqueous solution via solid or liquid phase organosynthesis as monomers attached to a superacid solution in structures such as $HF-SbF_5SO_2$. Such materials can be isolated only in extremely low concentration and decompose readily upon isolation.

In contrast, the stable hydronium material as disclosed herein that is employed in the cosmetic composition provides a source of concentrated hydronium ions that are long lasting and can be subsequently isolated from solution if desired or required.

In certain embodiments, the compound that is present in the cosmetic composition, when present in polar solution can have the following chemical structure:

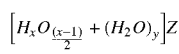

wherein x is and odd integer between 3-11;
y is an integer between 1 and 10; and
Z is a polyatomic or monoatomic ion.

The cosmetic composition as disclosed herein can also include at least one carrier material. Where desired or required the cosmetic composition can include at least one active ingredient.

The polyatomic ion in the compound as disclosed can be derived from an ion that is derived from an acid having the ability to donate on or more protons. The associated acid can be one that would have a $pK_a$ values $\geq 1.7$ at 23° C. The ion employed can be one having a charge of +2 or greater. Non-limiting examples of such ions include sulfate, carbonate, phosphate, oxalate, chromate, dichromate, pyrophosphate and mixtures thereof. In certain embodiments, it is contemplated that the polyatomic ion can be derived from mixtures that include polyatomic ion mixtures that include ions derived from acids having $pK_a$ values $\leq 1.7$.

The stable electrolyte material as disclosed herein is stable at standard temperature and pressure and can exist as an oily liquid. The electrolyte material can be added to water or other polar solvent to produce a polar solution that contains an effective concentration of stable hydronium ion that is greater than 1 part per million.

It has been found, quite unexpectedly, that the hydronium ions derived from the addition of the stable electrolyte material disclosed herein alter the acid functionality of the resulting solvent without the concomitant alteration of the free to total acid ratio. The alteration in acid functionality can include characteristic such as change in measured pH, changes in free-to-total acid ratio, changes specific gravity change and rheology. Changes in spectral and chromatography output are also noted as compared to the incumbent acid materials used in production of the stable electrolyte material containing the initial hydronium ion complex. Addition of the stable hydronium ion material as disclosed herein results in changes in $pK_a$ which do not correlate to the changes observed in free-to-total acid ratio.

Thus, the addition of the stable hydronium electrolyte material as disclosed herein to a polar component incorporated in the cosmetic composition such as an aqueous solution having a pH between 6 and 8 results in a solution having an effective $pK_a$ between 0 to 5. It is also to be understood that $K_a$ of the resulting solution can and a value less than zero as when measured by a calomel electrode, specific ion ORP probe such as the Thermo-Scientific Orion Star A-211. As used herein the term "effective $pK_a$" is a measure of the total available hydronium ion concentration present in the resulting solvent such as the aqueous component that is incorporated in the cosmetic composition. Thus, it is possible that pH and/or associated $pK_a$ of a material to which that stable hydronium electrolyte material is added, when measured may have a numeric value represented between −3 and 7.

Typically, the pH of a solution is a measure of its proton concentration or is the inverse proportion of the —OH moiety. It is believed that the stable electrolyte material as disclosed herein, when introduced into a polar solution, facilitates at least partial coordination of hydrogen protons with the hydronium ion electrolyte material and/or its associated lattice or cage. As such, the introduced stable hydronium ion exists in a state that permits selective functionality of the introduced hydrogen associated with the hydrogen ion.

More specifically, the stable electrolyte material as disclosed herein can have the general formula:

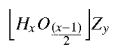

x is and odd integer ≥3;
y is an integer between 1 and 20; and
Z is one of a monoatomic ion from Groups 14 through 17 having a charge between −1 and −3 or a polyatomic ion having a charge between −1 and −3.

In the composition of matter as disclosed herein, monatomic constituents that can be employed as Z include Group 17 halides such as fluoride, chloride, iodide and bromide; Group 15 materials such as nitrides and phosphides and Group 16 materials such as oxides and sulfides. Polyatomic constituents include carbonate, hydrogen carbonate, chromate, cyanide, nitride, nitrate, permanganate, phosphate, sulfate, sulfite, chlorite, perchlorate, hydrobromite, bromite, bromate, iodide, hydrogen sulfate, hydrogen sulfite. It is contemplated that the composition of matter can be composed of a single one to the materials listed above or can be a combination of one or more of the compounds listed.

It is also contemplated that, in certain embodiments, x is an integer between 3 and 9, with x being an integer between 3 and 6 in some embodiments.

In certain embodiments, y is an integer between 1 and 10; while in other embodiments, y is an integer between 1 and 5.

The composition of matter as disclosed herein can have the following formula, in certain embodiments:

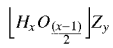

x is and odd integer between 3 and 12;
y is an integer between 1 and 20; and
Z is one of a group 14 through 17 monoatomic ion having a charge between −1 and −3 or a polyatomic ion having a charge between −1 and −3 as outlined above. With some embodiments having x between 3 and 9 and y being an integer between 1 and 5.

It is contemplated that the composition of matter exists as an isomeric distribution in which the value x is an average distribution of integers greater than 3 favoring integers between 3 and 10.

The composition of matter as disclosed herein can be formed by the addition of a suitable inorganic hydroxide to a suitable inorganic acid. The inorganic acid may have a density between 22° and 70° Baume; with specific gravities between about 1.18 and 1.93. In certain embodiments, it is contemplated that the inorganic acid will have a density between 50° and 67° Baume; with specific gravities between 1.53 and 1.85. The inorganic acid can be either a monoatomic acid or a polyatomic acid.

The inorganic acid and be homogenous or can be a mixture of various acid compounds that fall within the defined parameters. It is also contemplated that the acid may be a mixture that includes one or more acid compounds that fall outside the contemplated parameters but in combination with other materials will provide an average acid composition value in the range specified. The inorganic acid or acids employed can be of any suitable grade or purity. In certain instances, tech grade and/or food grade material can be employed successfully.

In preparing the stable electrolyte material as disclosed herein, the inorganic acid can be contained in any suitable reaction vessel in liquid form at any suitable volume. In various embodiments, it is contemplated that the reaction vessel can be non-reactive beaker of suitable volume. The volume of acid employed can be a small as 50 ml. Larger volumes up to and including 5000 gallons or greater is within the purview of this disclosure.

The inorganic acid can be maintained in the reaction vessel at a temperature that is generally ambient. It is possible to maintain the initial inorganic acid temperature can be maintained in a range between approximately 23° and about 70° C. However lower temperatures in the range of 15° and about 40° C. can also be employed.

The inorganic acid is mechanically agitated by suitable means to impart mechanical energy at a level between approximately 0.5 HP and 3 HP with agitation levels imparting mechanical energy between 1 and 2.5 HP being employed in certain applications of the process. Agitation can be imparted by a variety of suitable means including but not limited to DC servodrive, electric impeller, magnetic stirrer, chemical inductor, and the like.

Agitation can commence at an interval immediately prior to hydroxide addition and can continue for an interval during at least a portion of the hydroxide introduction step.

In the process as disclosed herein, the acid material of choice may be a concentrated acid with an average molarity (M) of at least 7 or above. In certain procedures, the average molarity will be at least 10 or above; with an average molarity between 7 and 10 being useful in certain applications. The acid of employed may exist and a pure liquid, a liquid slurry or as an aqueous solution of the dissolved acid in essentially concentrated form.

Suitable acid materials can be either aqueous or non-aqueous materials. Non-limiting examples of suitable acid materials can include one or more of the following: hydrochloric acid, nitric acid, phosphoric acid, chloric acid, perchloric acid, chromic acid, sulfuric acid, permanganic acid, prussic acid, bromic acid, hydrobromic acid, hydrofluoric acid, iodic acid, fluoboric acid, fluosilicic acid, fluotitanic acid.

In certain embodiments, the defined volume of a liquid concentrated strong acid employed can be sulfuric acid having a specific gravity between 55° and 67° Baume. This material can be placed can be place in the reaction vessel and mechanically agitated at a temperature between 16° and 70° C.

In certain specific applications of the method disclosed a measured, defined quantity of suitable hydroxide material can added to an agitating acid, such as concentrated sulfuric acid that is present in the beaker in a measured, defined amount. The amount of hydroxide that is added will be that sufficient to produce a solid material that is present in the composition as a precipitate and/or a suspended solids or colloidal suspension. The hydroxide material employed can be a water-soluble or partially water-soluble inorganic hydroxide. Partially water-soluble hydroxides employed in the process will generally be those which exhibit miscibility with the acid material to which they are added. Non-limiting examples of suitable partially water-soluble inorganic hydroxides will be those that exhibit at least 50% miscibility in the associated acid. The inorganic hydroxide can be either anhydrous or hydrated.

Non-limiting examples of water-soluble inorganic hydroxides include water soluble alkali metal hydroxides, alkaline earth metal hydroxides and rare earth hydroxides; either alone or in combination with one another. Other hydroxides are also considered to be within the purview of this disclosure. "Water-solubility" as the term is defined in conjunction with the hydroxide material that will be employed is defined a material exhibiting dissolution characteristics of 75% or greater in water at standard temperature and pressure. The hydroxide that is utilized typically is a liquid material that can be introduced into the acid material as a true solution, a suspension, or a super-saturated slurry. In certain embodiments, it is contemplated that the concentration of the inorganic hydroxide in aqueous solution can be dependent on the concentration of the associated acid. Non-limiting examples of suitable concentrations for the hydroxide material are hydroxide concentrations greater than 5 to 50% of a 5-mole material.

Suitable materials include, but are not limited to, lithium hydroxide, sodium hydroxide, potassium hydroxide, ammonium hydroxide, calcium hydroxide, strontium hydroxide, barium hydroxide, magnesium hydroxide, and/or silver hydroxide. Inorganic hydroxide solutions, when employed may have concentration of inorganic hydroxide between 5 and 50% of a 5-mole material with concentration between 5 and 20% in certain applications. The inorganic hydroxide material, in certain processes, can be calcium hydroxide in a suitable aqueous solution such as present as slaked lime.

In the process as disclosed, the inorganic hydroxide in liquid or fluid form is introduced into the agitating acid material in one or more metered volumes over a defined interval to provide a defined resonance time. The resonance time in the process as outlined is considered to be the time interval necessary to promote and provide the environment in which the hydronium ion material develops. The resonance time interval as employed herein is typically between 12 and 120 hours with resonance time intervals between 24 and 72 hours and increments therein being utilized in certain applications.

In various applications of the process, the inorganic hydroxide is introduced into the acid at the upper surface in a plurality of metered volumes. Typically, the total amount of inorganic hydroxide material will be introduced as a plurality of measured portions over the resonance time, with front-loaded metered addition being employed in many instances. "Front-loaded metered addition" as the term is used herein is taken to mean addition of the total hydroxide volume over an initial percentage of the desired resonance time. Initial percentage values are considered to be between the first 25% and 50% of the total resonance time.

It is to be understood that the proportion of each metered volume that is added can be the same or can vary based on such non-limiting factors as external process conditions, in situ process conditions, specific material characteristics, and the like. It is contemplated that the number of metered volumes can be between 3 and 12. The interval between additions of each metered volume can be between 5 and 60 minutes in certain applications of the process as disclosed. The actual addition interval can be between 60 minutes to five hours.

In certain applications of the process, a 100 ml volume of 5% weight per volume of calcium hydroxide material is added to 50 ml of 66° Baume concentrated sulfuric acid in 5 metered increments of 2 ml per minute, optionally with admixture. Addition of the hydroxide to the sulfuric acid results in increasing liquid turbidity that evidences production of calcium sulfate solids as precipitate that is removed in a fashion coordinated with continued hydroxide addition in order to provide a minimum concentration of suspended and dissolved solids.

Without being bound to any theory, it is believed that the addition of calcium hydroxide to sulfuric acid results in the consumption of the initial hydrogen proton or protons associated with the sulfuric acid resulting in hydrogen proton oxygenation such that the proton in question is not off-gassed as would be generally expected upon hydroxide addition, but rather is recombined with ionic water molecule components present in the liquid material.

After the suitable resonance time as defined, the material, as it is produced, is subjected to a non-bi-polar magnetic field at a value greater than 2000 gauss; with magnetic fields great than 2 million gauss being employed in certain applications. It is contemplated that a magnetic field between 10,000 and 2 million gauss can be employed in certain situations. One non-limiting example of a suitable magnetic field generator is found in U.S. Pat. No. 7,122,269 to Wurzburger, the specification of which is incorporated by reference herein.

As desired, solid material present as precipitate or suspended solids can be removed by any suitable means. Such means include but need not be limited to the following: gravimetric, forced filtration, centrifuge, reverse osmosis and the like.

The composition of matter as disclosed herein is a shelf-stable viscous liquid that is believed to be stable for at least one year when stored at ambient temperature and 50 to 75% relative humidity. The composition of matter can be use neat in various end use applications. The composition of matter can have a 1.87 to 1.78 molar solution that contains 8 to 9% of the total moles of acid protons that are not charged balanced.

The stable electrolyte composition of matter which results from the process as disclosed has molarity of 200 to 150 M strength, and 187 to 178 M strength in certain instances, when measured titrametrically though hydrogen coulometry and via FFTIR spectral analysis. The material has a gravimetric range greater than 1.15; with ranges greater than 1.9 in in certain instances. The material when analyzed can be shown to yield up to1300 volumetric times of orthohydrogen per cubic ml versus hydrogen contained in a mole of water.

It is also contemplated that the composition of matter as disclosed can be introduced into a polar solvent and will result in a solution having concentration of hydronium ions greater than 15% by volume. In some applications, the concentration of hydronium ions can be greater than 25% and it is contemplated that the concentration of hydronium ions can be between 15 and 50% by volume.

The polar solvent can be either aqueous, or a mixture of aqueous and organic materials In situations where the polar solvent includes organic components, it is contemplated that the organic component can include at least one of the following: saturated and/or unsaturated short chain alcohols having less than 5 carbon atoms, and/or saturated and unsaturated short chain carboxylic acids having less than 5 carbon atoms. Where the solvent comprises water and organic solvents, it is contemplated that the water to solvent ratio will be between 1:1 and 400:1, water to solvent, respectively.

The ion complex that is present in the solvent material as describes herein may have any suitable structure and solvation that is generally stable and capable of functioning as an oxygen donor in the presence of the environment created to generate the same. In particular embodiments, the ion is depicted by the following formula:

$$\left[H_xO_{\frac{(x-1)}{2}}\right]+$$

wherein x is an odd integer ≥3.

It is contemplatedthation as defined herein exists in unique ion complexes having greater than seven hydrogen atoms in each individual ion complex which are referred to in this disclosure as hydronium ion complexes. As usedherein the term "hydroniumion complex" can be broadly defined as the cluster of molecules that surround the cation $H_xO_{x-1}+$ where x is an integer greater than or equal to 3. The hydronium ion complex may include at least four additional hydrogen molecules and a stoichiometric proportion of oxygen molecules complexed thereto as water molecules. Thus, the formulaic representation of non-limiting examples of the hydronium ion complexes that can be employed in the process herein can be depicted by the formula:

$$\left[H_xO_{\frac{(x-1)}{2}} + (H_2O)_y\right]$$

where x is an odd integer of 3 or greater; and
y is an integer from 1 to 20, with y being an integer between 3 and 9 in certain embodiments.

In various embodiments disclosed herein, it is contemplated that at least a portion of the hydronium ion complexes will exist as solvated structures of hydronium ions having the formula $$H_{5+x}O_{2y}+$$

wherein x is an integer between 1 and 4; and
y is an integer between 0 and 2.
In such structures, an $$\left[H_xO_{\frac{(x-1)}{2}}\right]+$$

core is protonated by multiple H₂O molecules. It is contemplated that the hydronium complexes present in the composition of matter as disclosed herein can exist as Eigen complex cations, Zundel complex cations or mixtures of the two. The Eigen solvation structure can have the hydronium ion at the center of an $H_9O_4+$ structure with the hydronium complex being strongly bonded to three neighboring water molecules. The Zundel solvation complex can be an $H_5O_2+$ complex in which the proton is shared equally by two water molecules. The solvation complexes typically exist in equilibrium between Eigen solvation structure and Zundel solvation structure. Heretofore, the respective solvation structure complexes generally existed in an equilibrium state that favors the Zundel solvation structure.

The present disclosure is based, at least in part, on the unexpected discovery that stable materials can be produced in which hydronium ion exists in an equilibrium state that favors the Eigen complex. The present disclosure is also predicated on the unexpected discovery that increases in the concentration of the Eigen complex in a process stream can provide a class of novel enhanced oxygen-donor oxonium materials.

The process stream as disclosed herein can have an Eigen solvation state to Zundel solvation state ratio between 1.2 to 1 and 15 to 1 in certain embodiments; with ratios between 1.2 to 1 and 5 to 1 in other embodiments.

The novel enhanced oxygen-donor oxonium material as disclosed herein can be generally described as a thermodynamically stable aqueous acid solution that is buffered with an excess of proton ions. In certain embodiments, the excess of protons ions can be in an amount between 10% and 50% excess hydrogen ions as measured by free hydrogen content.

It is contemplated that oxonium complexes employed in the process discussed herein can include other materials employed by various processes. Non-limiting examples of general processes to produce hydrated hydronium ions are discussed in U.S. Pat. No. 5,830,838, the specification of which is incorporated by reference herein.

The composition disclosed herein has the following chemical structure:

$$\left[H_xO_{\frac{(x-1)}{2}} + (H_2O)_y\right]Z$$

wherein x is an odd integer ≥3;
y is an integer between 1 and 20; and
Z is a polyatomic or monoatomic ion.

The polyatomic ion employed can be an ion derived from an acid having the ability to donate one or more protons. The associated acid can be one that would have a $pK_a$ values ≥1.7 at 23° C. The ion employed can be one having a charge of +2 or greater. Non-limiting examples of such ions include sulfate, carbonate, phosphate, chromate, dichromate, pyrophosphate and mixtures thereof. In certain embodiments, it is contemplated that the polyatomic ion can be derived from mixtures that include polyatomic ion mixtures that include ions derived from acids having $pK_a$ values ≤1.7.

In certain embodiments, the composition of matter can have the following chemical structure:

$$\left[H_xO_{\frac{(x-1)}{2}} + (H_2O)_y\right]Z$$

wherein x is an odd integer between 3-11;
y is an integer between 1 and 10; and
Z is a polyatomic ion The polyatomic ion can be derived from an ion derived from an acid having the ability to donate on or more protons. The associated acid can be one that would have a $pK_a$ values ≥1.7 at 23° C. The ion employed can be one having a charge of +2 or greater. Non-limiting examples of such ions include sulfate, carbonate, phosphate, oxalate, chromate, dichromate, pyrophosphate and mixtures thereof. In certain embodiments, it is contemplated that the polyatomic ion can be derived from mixtures that include polyatomic ion mixtures that include ions derived from acids having $pK_a$ values ≤1.7.

In certain embodiments, the composition as disclosed is composed of a stoichiometrically balanced chemical composition of at least one of the following: hydrogen (1+), triaqua-µ3-oxotri sulfate (1:1); hydrogen (1+), triaqua-µ3-oxotri carbonate (1:1), hydrogen (1+), triaqua-µ3-oxotri phosphate, (1:1); hydrogen (1+), triaqua-µ3-oxotri oxalate (1:1); hydrogen (1+), triaqua-µ3-oxotri chromate (1:1) hydrogen (1+), triaqua-µ3-oxotri dichromate (1:1), hydrogen (1+), triaqua-µ3-oxotri pyrophosphate (1:1), and mixtures thereof. It is understood that that composition as disclosed can be articulated as a stoichiometrically balanced chemical composition of at least one of the following: hydrogen, triaqua-µ3-oxotri sulfate; hydrogen, triaqua-µ3-oxotri carbonate; hydrogen, triaqua-µ3-oxotri phosphate; hydrogen, triaqua-µ3-oxotri oxalate; hydrogen, triaqua-µ3-oxotri chromate; hydrogen, triaqua-µ3-oxotri dichromate; hydrogen, triaqua-µ3-oxotri pyrophosphate; and mixtures thereof, where in the components of the stoichiometrically balanced chemical compound are present in a 1:1 ratio.

It is also contemplated that the composition may contain alkaline oxonium ion derived complexes. As defined herein "alkaline oxonium ion complexes" are generally defined as negative oxygen anion having at least one trivalently bonded oxygen when the molecule is present as its basic salt. In certain embodiments the oxygen anion will exist in aqueous solution as a population predominantly composed of atoms having four, five and/or six hydrogen atoms bonded to a number of oxygen atoms that is at least one less than the number of hydrogens present.

When the composition of matter as disclosed herein is admixed with an aqueous or polar solvent, the resulting composition is as solution canbecomposedof basic or alkaline hydronium ions, basic or alkaline hydronium ion complexes and the like. Suitable anionic materials can also be referredto as alkaline hydroxoniumioncomplexes. The composition of matter and solutions that contain the same may have utility in various applications where elevated or alkaline pH is desirable. The materials disclosed herein may also have applicability situations not limited to certain cleaning and sanitizing applications.

It has been theorized that extreme trace amounts of anionic hydronium may spontaneously form in water from water molecules in the presence of free hydroxyl radicals. Without being bound to any theory, it is believed that naturally occurring stable anionic hydronium ions are extremely rare, if they occur at all. The concentration of naturally occurring anionic hydronium ions in water is estimated to be no more than 1 in 480,000,000. It is also theorized that naturally occurring anionic hydronium ions are unstable transient species with lifespans typically in the range of nanoseconds. Naturally occurring anionic hydronium ions are reactive and are readily solvated by water and, as such, these anionic hydronium ions do not exist in a free state.

When introduced into pure water, the stable anionic material disclosed herein will complex with water molecules to form unique hydration cages of various geometries, non-limiting examples of which will be described in greater detail subsequently. The alkaline electrolyte material as disclosed herein, when introduced into aqueous solution or polar solvent is stable and can be isolated from the associated aqueous solution or polar solvent by processes that will be described in detail subsequently.

The amphoteric cationic component can be an ion typically derived from one or more strong inorganic acids. Non-limiting examples of suitable strong inorganic acids are those having a $pK_a \geq 1.74$, which, when added to water, will ionize completely in an aqueous solution. Weaker acids, such as those having a $pK_a < 1.74$, when added to water, will achieve less than complete ionization in aqueous solution but may have utility in certain applications.

In the present disclosure, it has been found quite unexpectedly that the stable alkaline hydronium electrolyte material as defined herein, when added to an aqueous solution, will produce a polar solvent and provide and effective $pK_a$ which is dependent on the amount of stable alkaline hydronium material added to the corresponding solution independent of the hydroxyl ion concentration originally present in that solution. The resulting solution can function as a polar solvent and can have an effective $pK_b$ between 7 and 14 in certain applications when the initial solution pH prior to addition of the stable alkaline hydronium material is between 6 and 8.

It is also contemplated that the stable anionic electrolyte material as disclosed herein can be added to solutions having an initial pH in the acidic ranges, for example between 2 and 6 to non-reactively adjust the pH of the resulting solution to neutral or alkaline levels and/or the effective or actual $pK_b$ of the resulting solution to levels between 7 and 14, with levels between 7 and 12 being achieved in certain applications. The stable anionic electrolyte material as disclosed herein can be added to an acidic material or solution of choice without measurable reactive properties including, but not limited to, exothermicity, oxidation or the like.

The acidity of any theoretical cationic hydronium ions existing in water as a result of aqueous auto-dissociation is the implicit standard used to judge the strength of an acid in water. Strong acids are considered better proton donors than the theoretical cationic hydronium ion material; otherwise a significant portion of introduced acid would exist in a non-ionized state. Strong bases are considered to be better or more efficient hydroxyl donors than the theoretic anionic hydronium material. As indicated previously, theoretical hydronium ions, either cationic and anionic, derived from aqueous auto-dissociation are unstable as species, random in occurrence and believed to exist, if at all in extreme low concentrations in an associated aqueous solution. Generally, cationic or anionic hydronium ions existing in aqueous solution will be present, if at all, in concentrations between 0 and 1 values less than 1 in 480,000,000. Cationic hydronium ions can be isolated, if at all, from native aqueous solution via solid or liquid phase organo-synthesis as monomers attached to a superacid ligand or solution in structures such as $HF-SbF_5SO_2$ in the case of cationic hydronium. To date, there has been no successful attempt yielding isolated stable anionic hydronium ion material. Thus, it can be concluded that isolation of cationic and/or anionic hydronium materials can be accomplished, if at all, only in extremely low concentration and that any such isolated material decomposes readily upon isolation.

In contrast, the stable anionic hydronium material as disclosed herein, provides a source of concentrated anionic hydronium ions that has an extended shelf life and provides a long-lasting source of available anionic hydronium ion material when added to a solution such as water or a suitable polar solvent. The material disclosed herein maintains performance efficacy over extended or prolonged time periods.

In certain embodiments, the composition of matter, when present in polar or semi-polar solution can have the following chemical structure:

$$H_xO_{x-y}{}^{a-}Z^{b+}$$

wherein x is an integer greater than 3;
y is an integer less than x;

a is a value between 1 and 6;

b is a value between 1 and 3;

Z is a monoatomic cation, polyatomic cation or cationic complex.

The anion $H_xO_{x-y}{}^{a-}$ can be present in loose coordinated clustered relationship; forming stable hydration complexes.

The hydration complexes can have various geometries which can vary based on factors such as the value of x. One non-limiting geometry of the hydronium anion $H_4O_3{}^{2-}$ is depicted in FIG. 1. It is theorized that the hydronium anion $H_4O_3{}^{2-}$ will have two hydrogen atoms bonded to each respective oxygen atom in the anionic molecule with at least two of hydrogen atoms shared between two of the respective oxygen atoms. In the molecule depicted the alpha, beta and gamma oxygen atoms are sequentially oriented. The H—O—H bond angle for the beta oxygen is estimated to be between 105° to 108°; while the H—O—H bond angles for the alpha and gamma oxygen atoms are each estimated to be greater than 130° but less than 140°.

The polyatomic cation can be derived from a material having at least one amphoteric radical. In certain embodiments, the polyatomic cation employed can be an amphoteric cation having a charge of or greater. Non-limiting examples of such negative cations include sulfate, carbonate, phosphate, chromate, dichromate, polyphosphate, orthophosphate and mixtures thereof. In certain embodiments, it is contemplated that the amphoteric polyatomic cation can be derived from acids having $pK_a$ values ≤1.7.

The cation Z can be a monoatomic cation from the alkali, alkali earth metal, transition metals, post transition metals and the like. In certain embodiments, these monatomic cations can be Group 1 materials such as lithium, sodium, and potassium; Group 2 materials such as beryllium, magnesium, calcium, Group 4 materials such as titanium, Group 5 materials such as vanadium and niobium; Group 6 materials such as chromium and molybdenum; Group 7 material such as manganese; Group 8 materials such as iron; Group 9 materials such as cobalt; Group 10 materials such as nickel and palladium; Group 11 materials such as copper, silver and gold; Group 12 materials such as zinc and cadmium; and Group 13 materials such as aluminum.

In certain embodiments, the monoatomic cation Z will have a charge equal to or greater than +2. Non-limiting examples of such materials include the Group 2 materials as well as aluminum. Other cations that are contemplated include iron(III), iron(II), copper(II), cobalt(III), cobalt(II), tin(II), tin(IV), lead(II), lead(IV), mercury(II) and mercury (I).

Suitable cation complexes Z that can include boron-magnesium complexes such as boron-nickel, boron-lithium, magnesium-lithium, magnesium-silicon, and lithium-silicon. The cation employed can have a charge of +2 or greater in certain embodiments and applications.

In many situations, the stable alkaline electrolyte material as disclosed herein is stable at standard temperature and pressure and can exist as a water-like liquid having wetting characteristics less than water; i.e. less than 70 dynes/cm. The electrolyte material can be added to water or other polar solvents to produce a solution that contains an effective concentration of stable hydronium anion material in either the non-dissociated state, the dissociated state or a combination of the two that is greater than 1 part per million. In certain applications the electrolyte material can be present in concentrations greater than 0.5% by weight. It is contemplated that the alkaline electrolyte material can be present at concentration maximums up to between 10 to 1 mole ratio equivalents and 5 to 1 mole ratio equivalents. That is, it would take approximately 10 molar equivalents of a suitable standard inorganic acid, for example hydrochloric acid, to neutralize one mole of the material disclosed herein.

It has been found, quite unexpectedly, that the hydroniun anion derived from the addition of the stable alkaline electrolyte material disclosed herein alter the acid functionality of the resulting material without the concomitant alteration of the free to total acid ratio. The alteration in acid functionality can include characteristics such as changes in measured pH, changes in free-to-total acid ratio, changes in specific gravity and rheology. Changes in spectral and chromatography output are also noted as compared to the incumbent materials used in production of the stable alkaline electrolyte material that contains the alkaline hydronium ion complex disclosed herein. Addition of the stable hydronium ion material as disclosed herein results in changes in $pK_b$ which do not correlate to the changes that would be typically observed in free-to-total acid ratio.

Thus the addition of the stable alkaline hydronium electrolyte material as disclosed herein to an aqueous solution having a pH between 6 and 8 results in a solution having an effective $pK_b$ between 8 and 14. It is also to be understood that Kb of the resulting solution can exhibit a value greater than 14 when measured by a calomel electrode, specific ion ORP probe. As used herein the term "effective $pK_b$" is defined as a measure of the total available hydronium anion concentration present in the resulting solvent or solution and can be defined as the inverse reciprocal of $pK_a$. Given the performance characteristics of various probes and measurement devices, it is possible that pH and/or associated $pK_a$ of a material when measured may have a numeric value represented between 7 and 16.

Typically, the pH of a solution is a measure of its proton concentration or is the inverse proportion of the —OH moiety. It is believed that the stable alkaline electrolyte material disclosed herein, when introduced into a matrix such as a polar solution, facilitates at least partial coordination of hydrogen protons with the hydronium anion electrolyte material and/or its associated complex existing as complexes of one or more hydronium ion s in complex with one another. As such, the introduced stable hydronium anion exists in a state that permits selective functionality of the introduced hydroxyl moieties relative to other components present in the associated matrix such as the polar solution.

More specifically, the stable electrolyte material as disclosed herein can have the general formula:

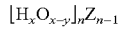

x is an integer ≤4;

y is an integer less than x;

n is an integer between 1 and 4; and

Z is an amphoteric polyatomic ion having a charge between +1 and +3.

Amphoteric polyatomic constituents include carbonate, hydrogen carbonate, chromate, cyanide, nitride, nitrate, permanganate, phosphate, sulfate, sulfite, chlorite, perchlorate, hydrobromite, bromite, bromate, iodide, hydrogen sulfate, hydrogen sulfite. It is contemplated that the composition of matter can be composed of a single one to the materials listed above or can be a combination of one or more of the compounds listed.

It is also contemplated that, in certain embodiments, x is an integer between 3 and 9, with x being an integer between 3 and 6 in some embodiments.

In certain embodiments, y is an integer having a value of y=1, and, where applicable, y=2 or y=3.

The composition of matter as disclosed herein can have the following formula, in certain embodiments:

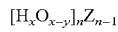

x is and odd integer between 4 and 6;
y is an integer less than x and between 1 and 3; and
Z is an amphoteric polyatomic ion having a charge between 1 and 3 and can be one of more of the following: carbonate, hydrogen carbonate, chromate, cyanide, nitride, nitrate, permanganate, phosphate, sulfate, sulfite, chlorite, perchlorate, hydrobromite, bromite, bromate, iodide, hydrogen sulfate, hydrogen sulfite.

It is contemplated that the composition of matter exists as an isomeric distribution in which the value x is an average distribution of integers greater than 3 favoring integers between 4 and 6.

The composition of matter as disclosed herein can be formed by the addition of a suitable inorganic acid to a suitable inorganic hydroxide. The inorganic acid may have a density between 22° and 70° Baume; with specific gravities between about 1.18 and 1.93. In certain embodiments, it is contemplated that the inorganic acid will have a density between 50° and 67° Baume; with specific gravities between 1.53 and 1.85. The inorganic acid can be either a monoatomic acid or a polyatomic acid.

The inorganic acid can be homogenous or can be a mixture of various acid compounds that fall within the defined parameters. It is also contemplated that the acid may be a mixture that includes one or more acid compounds that fall outside the contemplated parameters but in combination with other materials will provide an average acid composition value in the range specified. The inorganic acid or acids employed can be of any suitable grade or purity. In certain instances, tech grade and/or food grade material can be employed successfully.

The hydroxide material employed can be a water-soluble or partially water-soluble inorganic hydroxide. Partially water-soluble hydroxides employed in the process will generally be those which exhibit miscibility with the acid material to be added. Non-limiting examples of suitable partially water-soluble inorganic hydroxides will be those that exhibit at least 50% miscibility in the associated acid. The inorganic hydroxide can be either anhydrous or hydrated.

Non-limiting examples of water-soluble inorganic hydroxides include water soluble alkali metal hydroxides, alkaline earth metal hydroxides and rare earth hydroxides; either alone or in combination with one another. Other hydroxides are also considered to be within the purview of this disclosure. "Water-solubility" as the term is defined in conjunction with the hydroxide material that will be employed is defined a material exhibiting dissolution characteristics of 75% or greater in water at standard temperature and pressure. The hydroxide that is utilized typically is a liquid material that can be introduced into the acid material as a true solution, a suspension or super-saturated slurry. In certain embodiments, it is contemplated that the concentration of the inorganic hydroxide in aqueous solution can be dependent on the concentration of the associated acid. Non-limiting examples of suitable concentrations for the hydroxide material are hydroxide concentrations greater than 5 to 50% of a 5-mole material.

Suitable materials include, but are not limited to, lithium hydroxide, sodium hydroxide, potassium hydroxide, ammonium hydroxide, calcium hydroxide, strontium hydroxide, barium hydroxide, magnesium hydroxide, and/or silver hydroxide. Inorganic hydroxide solutions, when employed may have concentration of inorganic hydroxide between 5 and 50% of a 5-mole material with concentration between 5 and 20% in certain applications. The inorganic hydroxide material, in certain processes, can be calcium hydroxide in a suitable aqueous solution such as present as slaked lime.

In preparing the stable electrolyte material as disclosed herein, an inorganic base can be contained in any suitable reaction vessel in liquid form at any suitable volume. In various embodiments, it is contemplated that the reaction vessel can be non-reactive beaker of suitable volume. The volume of inorganic base that can be employed can be a small as 50 ml. Larger volumes up to and including 5000 gallons or greater are also considered to be within the purview of this disclosure.

The inorganic base can be maintained in the reaction vessel at a temperature that is generally ambient. It is possible to maintain the initial inorganic base temperature in a range between approximately 23° and about 70° C. However lower temperatures in the range of 15° and about 40° C. can also be employed.

The inorganic base can be mechanically agitated by suitable means to impart mechanical energy at a level between approximately 0.5 HP and 3 HP with agitation levels imparting mechanical energy between 1 and 2.5 HP being employed in certain applications of the process. Agitation can be imparted by a variety of suitable means including but not limited to DC servodrive, electric impeller, magnetic stirrer, chemical inductor and the like.

Agitation can commence at an interval immediately prior to acid addition and can continue for an interval during at least a portion of the acid introduction step.

The acid material that is to be introduced may be maintained in any suitable vessel from which the material can be dispensed in a measured metered manner. The vessel can include suitable heating elements if desired or required that are configured to provide heated material at a temperature between ambient and approximately 200° F.; with temperatures between ambient and 70° C. being employed in certain embodiments.

In the process as disclosed herein, the acid material of choice may be a concentrated acid with an average molarity (M) of at least 7 or above. In certain procedures, the average molarity will be at least 10 or above; with an average molarity between 7 and 10 being useful in certain applications. The acid of employed may exist and a pure liquid, a liquid slurry or as an aqueous solution of the dissolved acid in essentially concentrated form.

Suitable acid materials can be either aqueous or non-aqueous materials. Non-limiting examples of suitable acid materials can include one or more of the following: hydrochloric acid, nitric acid, phosphoric acid, chloric acid, perchloric acid, chromic acid, sulfuric acid, permanganic acid, prussic acid, bromic acid, hydrobromic acid, hydrofluoric acid, iodic acid, fluoboric acid, fluosilicic acid, fluotitanic acid.

In certain embodiments, the concentrated strong acid employed can be sulfuric acid having a specific gravity between 55° and 67° Baume. This material can be placed can be place in the reaction vessel and mechanically agitated at a temperature between 16° and 70° C.

In certain specific applications of the method disclosed a measured, a defined quantity of the suitable acid material can be added to a defined amount of agitating hydroxide that is present in the beaker. The amount of acid that is added will be that sufficient to produce a solid material that is present in the composition as a precipitate and/or a suspended solids or colloidal suspension.

In the process as disclosed, the acid material is added to the agitating inorganic hydroxide in one or more metered volumes over a defined interval to provide a defined resonance time. The resonance time in the process as outlined is considered to be the time interval necessary to promote and provide the environment in which the hydronium anion material develops. The resonance time interval as employed herein is typically between 12 and 120 hours with resonance time intervals between 24 and 72 hours and increments therein being utilized in certain applications.

In various applications of the process, the acid is introduced into the inorganic hydroxide at the upper surface in a plurality of metered volumes. Typically, the total amount of the acid material will be introduced as a plurality of measured portions over the associated resonance time, with front loaded metered addition being employed in many instances. "front-loaded metered addition" as the term is used herein is taken to mean addition of the total acid volume over an initial percentage of the desired resonance time. Initial percentage values are considered to be between the first 25% and 50% of the total resonance time.

It is to be understood that the proportion of each metered volume that is added can be the same or can vary based on such non-limiting factors as external process conditions, in situ process conditions, specific material characteristics, and the like. It is contemplated that the number of metered volumes can be between 3 and 12. The interval between additions of each metered volume can be between 5 and 60 minutes in certain applications of the process as disclosed. The actual addition interval can be between 60 minutes to five hours.

In certain applications of the process, a 100 ml volume of 66° Baume concentrated sulfuric acid material is added to 50 ml of 5% by weight calcium hydroxide in 5 metered increments of 2 ml per minute with admixture. Addition of the sulfuric acid to the calcium hydroxide results in increasing liquid turbidity that evidences production of calcium sulfate solids as precipitate that is removed in a fashion coordinated with continued acid addition in order to provide a minimum concentration of suspended and dissolved solids.

Without being bound to any theory, it is believed that the addition of sulfuric acid to calcium hydroxide results in the consumption of the initial hydrogen proton or protons associated with the introduced sulfuric acid resulting in hydrogen proton oxygenation such that the proton in question is not off-gassed as would be generally expected upon acid addition, but rather is recombined with ionic water molecule components present in the liquid material.

After completion of the suitable resonance time as defined, the material, as it is produced, is subjected to a non-bi-polar magnetic field at a value greater than 2000 gauss; with magnetic fields great than 2 million gauss being employed in certain applications. It is contemplated that a magnetic field between 10,000 and 2 million gauss can be employed in certain situations. One non-limiting example of a suitable magnetic field generator is found in U.S. Pat. No. 7,122,269 to Wurzburger, the specification of which is incorporated by reference herein.

As desired, solid material present as precipitate or suspended solid byproducts can be removed by any suitable means. Such means include but need not be limited to the following: gravimetric, forced filtration, centrifuge, reverse osmosis and the like.

The composition of matter as disclosed herein is a shelf-stable viscous liquid that is believed to be stable for at least one year when stored at ambient temperature and 50 to 75% relative humidity. The composition of matter can be use neat in various end use applications. The composition of matter can have a 1.87 to 1.78 molar solution that contains 8 to 9% of the total moles of acid protons that are not charged balanced.

The stable electrolyte composition of matter which results from the process as disclosed has molarity of 200 to 150 M strength, and 187 to 178 M strength in certain instances, when measured titrametrically though hydrogen coulometry and via FFTIR spectral analysis. The material has a gravimetric range greater than 1.15; with ranges greater than 1.9 in in certain instances. The material when analyzed can be shown to yield up to 1300 volumetric times of orthohydrogen per cubic ml versus hydrogen contained in a mole of water.

It is also contemplated that the composition of matter as disclosed can be introduced into a polar solvent and will result in a solution having concentration of hydronium anions greater than 15% by volume. In some applications, the concentration of hydronium anions can be greater than 25% and it is contemplated that the concentration of hydronium anions can be between 15 and 50% by volume.

The polar solvent can be either aqueous, or a mixture of aqueous and organic materials. In situations where the polar solvent includes organic components, it is contemplated that the organic component can include at least one of the following: saturated and/or unsaturated short chain alcohols having less than 5 carbon atoms, and/or saturated and unsaturated short chain carboxylic acids having less than 5 carbon atoms. Where the solvent comprises water and organic solvents, it is contemplated that the water to solvent ratio will be between 1:1 and 400:1, water to solvent, respectively.

The ion complex that is present in the solvent material as describes herein may have any suitable structure and solvation that is generally stable and capable of functioning as an oxygen donor in the presence of the environment created to generate the same. In particular embodiments, the ion is depicted by the following formula:

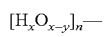

$[H_xO_{x-y}]_n{-}$ wherein x is an integer ≥4;
y is an integer less than x;
n is an integer between 1 and 4; and
Z is an amphoteric polyatomic ion having a charge between +1 and +3.

It is contemplatedthation as defined herein exists in unique anion complexes havingbetween 4 and 7 hydrogen atoms in complex with a lesser number of oxygen atoms in each individual anioncomplex which are referred to in this disclosure as hydronium anion complexes. As usedherein the term "hydronium anion complex" can be broadly defined as the cluster of molecules that surround the cation $H_xO_{x-y}{-}$ where x is an integer greater than or equal to 4. The hydronium anion complex may include at least four additional hydrogen molecules and a stoichiometric proportion of oxygen molecules complexed thereto as water molecules. Thus, the formulaic representation of non-limiting examples of the hydronium ion complexes that can be employed in the process herein can be depicted by the formula: In certain embodiments, the composition of matter is composed of a stoichiometrically balanced chemical hydrogen peroxide hydroxyl sulfate hydrate.

The cosmetic composition as disclosed herein can include at least one active agent. The at least one active agent can vary depending on the nature and end use of the cosmetic composition. In coloring cosmetics, the active ingredient can be a color additive or pigment of a desired particle size and hue. Such materials are those compounds approved by regulatory agencies such as the US Food and Drug Administration. Non-limiting examples of such materials as would be used in lipsticks include inorganic materials such as various iron oxides, titanium dioxide and zinc oxide as well as organic colors such as reds (Red 6, 7, and 21), yellows (such as Yellow 6), oranges (such as Orange 5 in concentrations less than 5%) and lakes such as Red 7 Lake and Yellow 5 Lake. It can also include special effect pigments such as micas coated with iron oxides and titanium dioxide and bismuth oxychloride.

Such lip color colorant materials such as those used in lipsticks can be maintained in dispersion in the carrier material which in lip colorant dispersion materials can be one or more waxes present alone or in combination with various oils, fats or butters. Non-limiting examples of suitable waxes include beeswax, candelilla wax, carnauba wax, paraffin wax, ozokerite wax, microcrystaline wax, polyethylene and lanolin alcohol. Non-limiting examples of oils, fats and butters include plant oils such as castor oil, grapeseed oil, almond oil, meadowfoam oil, olive oil, coconut oil, palm oil and various triglycerides. Non-limiting examples of butters include avocado butter, shea butter, and cocoa butter. Non-limiting examples of fatty acid esters such as isopropyl myristate, isopropyl palmitate, isostearyl isostearate and butyl stearate. Non-limiting examples of hydrocarbons and/or silicone that can be used include polyisobutene, mineral oil, petrolatum, isododecane and isoeicosane as well as cyclomethicone and dimethicone.

The cosmetic composition, when employed as a lip colorant can also contain a material having the composition according to equation I or equation II:

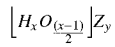

$$\left[ H_x O_{\frac{(x-1)}{2}} \right] Z_y \qquad \text{I}$$

wherein x is an odd integer ≥3;
y is an integer between 1 and 20; and
Z is one of a monoatomic ion from Groups 14 through 17 having a charge value between −1 and −3 or a polyatomic ion having a charge between −1 and −3; or

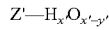

$$Z'{-}H_{x'}O_{x'-y'} \qquad \text{II}$$

wherein x' is an integer greater than 3
y' is an integer less than x'; and
Z' is one of a monoatomic cation, a polyatomic ion or a cationic complex; and at least one of a pigment, humectant, emollient, aqueous carrier, or the like.

It has been found, quite unexpectedly that the lip colorant composition having between 0.25% and 30% by weight of the foregoing composition have the formula of equation I or equation II exhibits resistance to microbial contamination.

In coloring cosmetics such as eye makeup products, the colorant or active ingredient can be a colorant as mentioned previously that can be dispersed in a suitable carrier such as a solvent. Non-limiting examples of solvents include water, glycerin, propylene glycol as sorbitol that can be present alone or in combination with suitable thickeners, structurants, emulsifiers and the like. The coloring cosmetic also includes between 0.025% and 30% by weight of the composition of Equation I or Equation II. Without being bound to any theory, it is believed that the presence of this compound contributes to preserve the associated composition protect against microbial contamination.

In certain embodiments, the cosmetic composition can be configured as a lotion or cream suitable for use as a component in a moisturizer, conditioner, cleanser composition, lotion or the like.

In constructing the cosmetic composition as disclosed herein, a foundational component can be produced that comprises an organic constituent in admixture with a polar component, in certain embodiments, an aqueous component. the organic constituent can include an oil-based thickener component that can include one or more of C-4 to C-30 branched or unbranched fatty alcohols, C-6 to C-30 fatty acids. The composition can also contain an effective concentration of emulsifier material. In certain embodiments, the emulsifier can be a suitable non-PEG emulsifiers including, but not limited to, ceteraryl olivate, stearyl olivate, ceterostearyl olivate, sorbitan olivate and the like, as well as triglycerides and the like.

Such thickener materials may function variously as emollients adjuvants and the like when in composition. In certain embodiments, it is contemplated that the cosmetic composition will contain between 2 to 10% by volume one or more fatty alcohols, such as C-8 to C-28 fatty alcohols. In some embodiments, the concentration of 2 and 5 volume %; while in some compositions, the concentration can be between 3.5 and 4.5 volume %. Non-limiting examples of such fatty alcohols suitable for use in the composition as disclose herein include cetyl alcohol, stearyl alcohol, and the like.

The non-PEG emulsifier component of the cosmetic composition as disclosed herein can be present in an amount between 1 and 7 volume % in certain embodiments, while in certain embodiments, the concentration of non-PEG emulsifier can be present in an amount between 2 and 4 volume %. Suitable non-PEG emulsifiers can be materials that function as surface modifiers. The suitable non-PEG emulsifier can be on that is derived from suitable food oils and the like. Suitable food oils can include, but are not limited to, materials that have elevated percentages of mono-unsaturated lipidic chains with percentages greater than 20% in certain applications. Non-limiting examples of suitable oils include olive oil, corn oil, soya oil, sunflower oil, peanut oil and the like. Without being bound to any theory, it is believed that the non-PEG emulsifier is derived from an oil component that includes one or more of the following: oleic acid, linoleic acid, linolenic acid, mysteric acid, palmetic acid, palmitoleic acid, hetadecanoic acid, stearic acid, linoleic acid, arachidic acid, gadoleic acid, behenic acid and the like. In certain embodiments, the suitable on-PEG emulsifier can be materials can be one or more of cetaryl olivate, sorbitan olivate and the like.

The cosmetic composition can also include glycerides, suitable esters derived from fatty glycerol and suitable fatty acids. In certain embodiments, the component can be composed of one or more triglyceride compounds in which the triglyceride is derived from one or more of fatty acids such as palmitic acid, oleic acid, linoleic acid, caprylic acid, capric acid and the like. In certain embodiments, the triglyceride component can be present as a combination of triglyceride materials such as caprylic triglycerides and capric triglycerides. It is also contemplated that the triglyceride material can be a caprylic/capric triglyceride which is believed to be a mixed triester derived from coconut oil and glycerin. The triglyceride component can be present in a concentration between 3 and 9 volume %, with volumes between about 5 and 6.5 volume % being employed in certain embodiments.

The organic constituent can also include a natural fatty acid component such as material derived from seed oils. The natural fatty acid component can be present in the composition in an amount between 0.5 volume % and 5 volume % with volumes between 1% and 3.5% in certain embodiments. Non-limiting examples of suitable seed oils that can be employed in the cosmetic composition disclosed herein include one or more of the following: almond oil, argan oil, borage oil, canola oil, corn oil, castor oil, cotton oil, linseed oil, grape seed oil, sesame oil, safflower oil, neem oil, sunflower oil, tung oil, macadamia oil, walnut oil. In certain embodiments, the natural seed oil can contain macadamia nut oil in an amount between 10% and 100% of the seed oil component of the cosmetic composition. Without being bound to any theory, it is believed that the fatty acid component derived from seed oil can be composed of unsaturated and/or saturated fatty acids having between 8 and 20 carbon atoms, with 8 to 20 carbon-atom mono-unsaturated and/or poly-unsaturated fatty acids being employed in certain applications.

The organic component can also contain at least one triterpenoid compound present in an amount between 4 and 6 volume % of the cosmetic composition. The triterpene employed can be composed of at least three units having the molecular formula $C_{30}H_{48}$. In certain embodiments, the triterpenoid compound can be at least one of squalene, malabaricane, isomalabaricane, polypodatetraene, lanostane, hopane, oleanane as well as derivatives of the foregoing. In certain embodiments, the triterpenoid compound employed is squalene, derivatives of squalene and mixtures thereof. Where derivatives of squalene are employed, suitable derivatives can include, but need not be limited to, saturated and partially saturated forms of squalene in which one or more of the double bonds has been eliminated. Naturally derived squalene can be extracted from cartilaginous fish such as sharks.

The cosmetic composition configured as a cream, lotion or the like will also contain an aqueous component that is made up of water. The water component can be composed of deionized, distilled water present in an amount sufficient to provide a finished cosmetic composition having a viscosity between about 200 to 500 cps. In certain embodiments, the aqueous component can be present in the composition at volumes between 50 and 75 volume % of the finished composition.

The composition will also contain the hydronium compound described herein at a concentration in an amount between about 0.1 and 2% by volume. In certain embodiments, the hydronium compound will be present in an amount between 0.1 and 15 by volume of the resulting formulation. The hydronium compound can be at least one of the following:

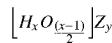

wherein x is and odd integer 3;
y is an integer between 1 and 20; and
Z is one of a monoatomic ion from Groups 14 through 17 having a charge value between −1 and −3 or a polyatomic ion having a charge between −1 and −3; or

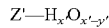

wherein x' is and integer greater than 3
y' is an integer less than x'; and
Z' is one of a monoatomic cation, a polyatomic ion or a cationic complex.

In certain embodiments, the hydronium ion can be a compound in which x' is an integer between 3 and 11. In certain embodiments, the hydronium ion can be a compound in which y is an integer between 1 and 10. In certain embodiments, the hydronium ion can be a compound in which the polyatomic ion has a charge of −2 or greater. In certain embodiments, the Z is selected from the group consisting of sulfate, carbonate, phosphate, oxalate, chromate, dichromate, pyrophosphate and mixtures thereof.

In certain embodiments, the cosmetic composition includes at least one of a stoichiometrically balanced chemical composition of at least one of the following: hydrogen (1+), triaqua-μ3-oxotri sulfate (1:1); hydrogen (1+), triaqua-μ3-oxotri carbonate (1:1), hydrogen (1+), triaqua-μ3-oxotri phosphate, (1:1); hydrogen (1+), triaqua-μ3-oxotri oxalate (1:1); hydrogen (1+), triaqua-μ3-oxotri chromate (1:1) hydrogen (1+), triaqua-μ3-oxotri dichromate (1:1), hydrogen (1+), triaqua-μ3-oxotri pyrophosphate (1:1), and mixtures thereof. It is understood that that composition as disclosed can be articulated as a stoichiometrically balanced chemical composition of at least one of the following: hydrogen, triaqua-μ3-oxotri sulfate; hydrogen, triaqua-μ3-oxotri carbonate; hydrogen, triaqua-μ3-oxotri phosphate; hydrogen, triaqua-μ3-oxotri oxalate; hydrogen, triaqua-μ3-oxotri chromate; hydrogen, triaqua-μ3-oxotri dichromate; hydrogen, triaqua-μ3-oxotri pyrophosphate; and mixtures thereof, where in the components of the stoichiometrically balanced chemical compound are present in a 1:1 ratio. Where desired or required, the cosmetic composition can include the aforementioned compound alone or in combination with additional basic hydronium compound having the following structure:

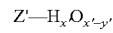

wherein x' is and odd integer ≥3;
y' is an integer between 1 and 20; and
Z is one of a monoatomic ion from Groups 14 through 17 having a charge value between −1 and −3 or a polyatomic ion having a charge between −1 and −3.

In certain embodiments the additional compound can be present in amounts between concentrations between about 5 to about 40 parts per 100 parts of the hydrogen(1+) triaqua compound. In certain embodiments, this basic hydronium compound will be one in which the monoatomic or polyatomic ion has a charge of −2 or greater. In certain embodiments, this basic hydronium compound will be one in which Z is selected from the group consisting of sulfate, carbonate, phosphate, oxalate, chromate, dichromate, pyrophosphate and mixtures thereof.

The cosmetic composition as disclosed herein may optionally contain additional components including but not limited to pigments, surfactants, thickeners and the like. It is also contemplated that the cosmetic composition as disclosed can be employed as a builder for additional compositions. In certain applications, it is contemplated that the composition may include one or more of the following: carriers such as glycerin between 2.5 and 3.5% by volume, rheology modifiers such as zanthan gum in amounts between 0.2 and 0.4 volume %, binders such as tapioca starch in amounts between 1.5 and 2.5 volume %.

Example I

In order to prepare a cosmetic composition as disclosed herein suitable qualities of cetaryl olivate, cetyl alcohol, and caprylic/caproic triglyceride are admixed with mild mixing with heating to provide a composition temperature of 80° C.

in initial quantities to provide final composition volumes of the respective components of 2% volume cetaryl olivate, 3.5% by volume cetyl alcohol, and 5.5% by volume caprylic/capric triglycerides. A quantity of squalene oil can be added to the mixture to provide a volume of squalene oil in the final cosmetic composition of 4% by volume. Additional quantities of nutritional seed oil can be added to the mixture to provide a finished composition concentration of seed oil of 2 volume %, with 1 volume % macadamia seed oil being added at a composition temperature of 80° C. Once the macadamia seed oil is added, the composition is permitted to cool to a temperature of 60° C. after which argan oil is added to provide a quantity in the final composition of 1% volume.

The resulting material has a viscosity between 5000 and 20,000 cps. Mixing progresses at a slow mixture speed with little to no shear and rotational speed between 100 and 200 rpm. Once the resulting organic mixture has cooled to a temperature of 60° C., the aqueous component can be added.

The aqueous component that is added is a deionized distilled water having a conductivity of 2.0 to 2.5 microseimens to which 0.5 to 1.0 volume % of the hydronium compound as described herein and commercially known as Tydronium from Tygrus of Troy Mich. is added to yield a pH as measured is between 1.5 to 2.0 as measured by a Thermo-Scientific Orion Star A-211 probe in which Ph is measured by a calomel ORP high sensitivity probe and a three point buffered standard at 2, 4 and 7. The resulting aqueous component is then back complexed with the basic hydronium derivative known as Trydroxide as disclosed herein and commercially available from Tygrus, of Troy Mich. at an amount of 40 parts Tydroxide to 100 parts Tydronium to provide a final pH at 3.5 to 4 measures as above at room temperature.

The resulting aqueous composition is added to the organic portion at a temperature between 40° and 70° C. in a volume to provide a finished composition of 60% water to 40% organic volume to volume in the finished composition. The resulting material is a white viscous creamy material having a viscosity between 300 cps and 500 cps and has a pH between 5 to 6.

Example II

In order to access the efficacy of the cosmetic compositions as disclosed a composition stabilized with the paraben compound methyl 4-hydroxybenzoate to assess product performance relative to the cosmetic composition as formulated in Example I. The paraben containing refence composition is prepared using the formulation process outlined in Example I substituting deionized distilled water in which the pH is adjusted using succinic acid in an amount sufficient to achieve a solution pH of 3.5 which will yield a succinic acid amount of 1.25 to 1.5 volume % in the finished composition. Because methyl paraben has limited solubility on water, the methyl paraben compound is pre-solubilized in a minor quantity of a compatible short chain alcohol such as ethyl alcohol prior to admixture into the associated aqueous-organic mixture. The resulting material is divided into sample portions for future analysis.

Example III

The material produced in Example I is evaluated to ascertain preservative and antimicrobial activity of the resulting composition and is compared to the reference material samples produced in Example II to determine physical performance.

Samples of the disclosed material and reference material are maintained in sealed and unsealed containers for intervals of four months one year and two years respectively. The sealed and unsealed test samples are also evaluated at respective humidity levels of 20% relative humidity, 50% relative humidity and 80% relative humidity. It is discovered that the reference material containing paraben material exhibited crystallization in unsealed containers at 4 months after placement in the container and at two years after packaging in the sealed container sample. In contrast, the material prepared per the method outlined in Example I shows no evidence of crystallization.

Portions of the resulting composition are divided in multiple containers to evaluate shelf stability at 4-month, one year, two year and temperature exposure. Reference samples and samples prepared per the method as outlined in Example I are placed in sealed and unsealed containers and are maintained at respective test temperatures of 20° C., 85° C. and 115° C. degradation of the reference samples is evidenced at approximately three months in some reference samples as early as one month exposure in the form of phase separation. In contrast, the material as disclosed herein evidences no indication of degradation.

Example IV

The antimicrobial effectiveness of the cosmetic material composition as disclosed herein and prepared according to the method outlined in Example I is ascertained using the methodology outlined in USP Presentative Effectiveness Testing Method and CTFA Method M-3). Representative predictive results are set forth in Table I.

TABLE I

| Organism | Innoc level | Day 7 | Day 14 | Day 21 | Day 28 | Pass/fail |
| --- | --- | --- | --- | --- | --- | --- |
| E coli ATCC 8739 | $6.0 \times 10^5$ | <10 | <10 | <10 | <10 | pass |
| S. aureus ATTC 5538 | $4. \times 10^5$ | <10 | <10 | <10 | <10 | pass |
| P. aeruinos ATCC 9027 | $9.0 \times 10^5$ | <10 | <10 | <10 | <10 | pass |
| C. Albicans ATCC 10231 | $6.0 \times 10^5$ | <10 | <10 | <10 | <10 | pass |
| A. brasiliesis ATCC 16404 | $3.0 \times 10^5$ | <10 | <10 | <10 | <10 | pass |

Samples of the cosmetic composition as outlined in Example I are retained at room temperature and relative humidity between 40% and 60% for one year and subjected to the tests outlined above> the results are outlined in Table II.

TABLE II

| Organism | Innoc level | Day 7 | Day 14 | Day 28 | Pass/fail |
|---|---|---|---|---|---|
| *E coli* ATCC 8739 | $6.0 \times 10^5$ | <10 | <10 | <10 | pass |
| *S. aureus* ATTC 5538 | $4. \times 10^5$ | <10 | <10 | <10 | pass |
| *P. aeruinos* ATCC 9027 | $9.0 \times 10^5$ | <10 | <10 | <10 | pass |
| *C. Albicans* ATCC 10231 | $6.0 \times 10^5$ | ~100,000 | ~50,000 | ~25,000 | pass |
| *A. brasiliesis* ATCC 16404 | $3.0 \times 10^5$ | ~10,000 | ~1.000 | ˋ700 | pass |

The cosmetic composition as disclosed herein prepared per the method outlined in Example I appears to exhibit extended antimicrobial activity without the presence of conventional preservatives. Without being bound to any theory, it is believed that this is due, at least in part, to the presence of the hydronium compound as defend herein.

Example V

In order to assess the efficacy of the cosmetic composition as disclosed herein, various compositions are prepared according to the process outlined in Example I. Anecdotal evidence supports the conclusion that the cosmetic composition when topically applied supports Indica of skin health that includes, but is not limited to one or more of increased elasticity and tone, wrinkle reduction, enhanced skin tone and color and/or reduction in localized inflammation. Without being bound to any theory, it is believed that this is due in part to the presence of increases levels of hydrogen topically delivered by the hydronium ion complex to regions of the epidermis, dermis and associated supportive tissue which supported cell metabolism.

Although embodiments have been described above regarding the accompanying drawings, those of skill in the art will appreciate that variations and modifications may be made without departing from the scope thereof as defined by the appended claims.

What is claimed is:

1. A composition comprising:
a component having the following chemical structure:

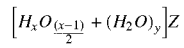

wherein x is and odd integer ≥3;
y is an integer between 1 and 20; and
Z is one of a monoatomic ion from Groups 14 through 17 having a charge value between −1 and −3 or a polyatomic ion having a charge between −1 and −3, wherein the composition is a cosmetic; and
at least one of a pigment, humectant, emollient, aqueous carrier or the like.

2. The composition of matter of claim 1 wherein the monoatomic or polyatomic ion has a charge of −2 or greater.

3. The composition of matter of claim 2 wherein Z is selected from the group consisting of sulfate, carbonate, phosphate, oxalate, chromate, dichromate, pyrophosphate and mixtures thereof.

4. The composition of matter of claim 1, wherein the component is composed of a stoichiometrically balanced chemical composition of at least one of the following: hydrogen, triaqua-µ3-oxotri sulfate; hydrogen, triaqua-µ3-oxotri carbonate, hydrogen, triaqua-µ3-oxotri phosphate; hydrogen, triaqua-µ3-oxotri oxalate; hydrogen, triaqua-µ3-oxotri chromate; hydrogen, triaqua-µ3-oxotri dichromate; hydrogen, triaqua-µ3-oxotri pyrophosphate; and mixtures thereof, where the components of the stoichiometrically balanced chemical compound are present in a 1:1 ratio.

5. The chemical formulation of claim 4 wherein the chemical composition is present in an about between about 0.05% and 50% by volumes.

6. The chemical formulation of claim 4 wherein the chemical composition is present in an amount sufficient to provide an effective pKa of between 0 and 5.

7. The chemical formulation of claim 4 wherein the chemical composition is present in an amount sufficient to provide an effective hydronium ion concentration between about 1 ppm and about 25% by volume.

8. The composition of matter of claim 1 wherein x is an integer between 3 and 11 and y is an integer between 1 and 10.

9. The composition of matter of claim 1 further comprising a polar solvent selected from the group consisting of water, short chain alcohols having between one and 4 carbon atoms and mixtures thereof.

10. The composition of claim 1 wherein the pigment is a colorant maintained in a dispersion in the carrier material.

* * * * *